(12) United States Patent
Berthier et al.

(10) Patent No.: US 8,022,030 B2
(45) Date of Patent: Sep. 20, 2011

(54) POLYMER CONJUGATES FOR A CONTROLLED RELEASE OF ACTIVE MOLECULES

(75) Inventors: Damien Berthier, Geneva (CH); Andreas Herrmann, Veyrier (CH)

(73) Assignee: Firmenich SA, Geneva (CH)

( * ) Notice: Subject to any disclaimer, the term of this patent is extended or adjusted under 35 U.S.C. 154(b) by 310 days.

(21) Appl. No.: 12/443,795

(22) PCT Filed: Oct. 5, 2007

(86) PCT No.: PCT/IB2007/054060
§ 371 (c)(1),
(2), (4) Date: Mar. 31, 2009

(87) PCT Pub. No.: WO2008/044178
PCT Pub. Date: Apr. 17, 2008

(65) Prior Publication Data
US 2010/0098649 A1    Apr. 22, 2010

(30) Foreign Application Priority Data
Oct. 10, 2006 (WO) ............. PCT/IB2006/053703

(51) Int. Cl.
| | | |
|---|---|---|
| A61K 8/00 | (2006.01) |
| A61K 8/18 | (2006.01) |
| A61Q 13/00 | (2006.01) |
| A61L 9/04 | (2006.01) |
| C08F 297/02 | (2006.01) |
| C08F 2/00 | (2006.01) |
| C08F 4/00 | (2006.01) |
| C08F 34/02 | (2006.01) |
| C08F 18/00 | (2006.01) |
| C08F 20/00 | (2006.01) |
| C08F 216/00 | (2006.01) |
| C08F 118/02 | (2006.01) |
| C08F 32/00 | (2006.01) |

(52) U.S. Cl. ........... 512/1; 512/4; 512/7; 512/8; 512/9; 512/14; 512/15; 512/16; 512/17; 512/18; 512/20; 512/22; 512/23; 512/24; 512/25; 512/26; 512/27; 525/242; 526/72; 526/89; 526/208; 526/214; 526/222; 526/234; 526/271; 526/292.3; 526/292.5; 526/307.4; 526/308; 526/319

(58) Field of Classification Search ............ 512/1, 4, 512/7, 8, 9, 14, 15, 16, 17, 18, 20, 22, 23, 512/24, 25, 26, 27; 525/242; 526/72, 89, 526/208, 214, 222, 234, 271, 292.3, 292.5, 526/308, 307.4, 319
See application file for complete search history.

(56) References Cited

U.S. PATENT DOCUMENTS

| | | | |
|---|---|---|---|
| 4,010,254 A | 3/1977 | Koulbanis et al. | 424/78 |
| 4,137,180 A | 1/1979 | Naik et al. | 252/8.8 |
| 5,236,615 A | 8/1993 | Trinh et al. | 252/174.11 |
| 6,315,987 B1 | 11/2001 | Plochocka | 424/49 |

FOREIGN PATENT DOCUMENTS

| | | |
|---|---|---|
| EP | 799 885 A1 | 10/1997 |
| WO | WO 97/34986 | 9/1997 |
| WO | WO 03/049666 | 6/2003 |
| WO | WO03049666 * | 6/2003 |

OTHER PUBLICATIONS

International Search Report PCT/IB2007/054060 Dated Feb. 11, 2008.
Berthier et al., "Amphiphilic Polymethacrylate- and Polystyrene-Based Chemical Delivery Systems for Damascones," Helvetica Chimica Acta, vol. 88, pp. 3089-3107 (2005).

* cited by examiner

Primary Examiner — Alexa Neckel
Assistant Examiner — Aaron Greso
(74) Attorney, Agent, or Firm — Winston & Strawn LLP

(57) ABSTRACT

The present invention relates to the field of perfumery. More particularly, it concerns co-polymers, derived from a maleic anhydride derivative and a ethylenic derivative, comprising at least one β-oxy or β-thio carbonyl moiety capable of liberating an active molecule such as, for example, an α,β-unsaturated ketone, aldehyde or carboxylic ester. The present invention concerns also the use of polymers or co-polymers in perfumery as well as the perfuming compositions or perfumed articles comprising the invention's compounds.

12 Claims, No Drawings

POLYMER CONJUGATES FOR A CONTROLLED RELEASE OF ACTIVE MOLECULES

This application is a 371 filing of International Patent Application PCT/IB2007/054060 filed Oct. 5, 2007.

TECHNICAL FIELD

The present invention relates to the field of perfumery. More particularly, it concerns co-polymers derived from a maleic anhydride derivative and comprising at least one β-oxy or β-thio carbonyl moiety capable of liberating an active molecule such as, for example, an α,β-unsaturated ketone, aldehyde or carboxylic ester. The present invention concerns also the use of polymers or co-polymers in perfumery as well as the perfuming compositions or perfumed articles comprising the invention's compounds.

PRIOR ART

The perfume industry has a particular interest for derivatives which are capable of prolonging the effect of active ingredients over a certain period of time, for example in order to overcome the problems encountered when using perfuming ingredients which are too volatile or have a poor substantivity. In particular, the industry is interested by derivatives capable of performing an improved olfactive performance. Said improvement can be in time, in intensity or in the effective amount of active compound released.

The patent application WO 03/049666 describes a class of compounds capable of prolonging the effect of active ingredients. Amongst these compounds there are mentioned polymers, citing as specific examples a few styrene co-polymers. However, although the performance described in the examples for several monomeric derivatives is quite good, the performance described for the styrene co-polymers is relatively modest (see examples 6 and 7 of the application). There is therefore still a need to improve the release properties of polymer based ingredients capable of prolonging the effect of active ingredients.

U.S. Pat. No. 6,315,987 describes a series of co-polymers releasing bacteriologically active alcohols, flavors or essential oils for oral care applications. Said co-polymers allow the release of alcohols via ester hydrolysis, but not the release of enone derivatives via an elimination reaction as described in the present invention. Furthermore, said prior art discloses an oral composition and does not suggest a perfuming composition that is quite a different medium. Moreover, the release by hydrolysis of esters is generally very slow in the absence of enzymes, particularly if esters of secondary alcohols are used and if they are directly grafted to the sterically demanding polymer backbone.

The invention's co-polymers are believed to have never been specifically disclosed or suggested in the prior art, nor their particular performances in the field of perfume release.

DESCRIPTION OF THE INVENTION

We have now surprisingly discovered the existence of particular polymers or co-polymers derived from a maleic anhydride derivative and comprising at least one β-oxy or β-thio carbonyl moiety capable of liberating an active molecule, namely an enone, and having superior performance when compared with the prior art ones. As "active molecule" we mean here any molecule capable of bringing an odor benefit or effect into its surrounding environment, and in particular an odoriferous molecule, i.e. a perfuming ingredient, such as an α,β-unsaturated ketone, aldehyde or carboxylic ester.

Said polymers or co-polymers can be used as perfuming ingredients.

A first object of the present invention concerns a co-polymer, capable of releasing in a controlled manner an odoriferous α,β-unsaturated ketone, aldehyde or carboxylic ester, and comprising at least one repeating unit of formula

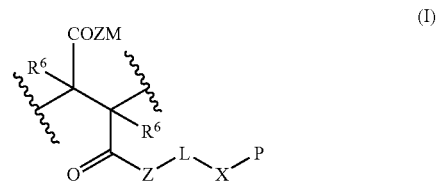

(I)

wherein

P represents a radical susceptible of generating an odoriferous α,β-unsaturated ketone, aldehyde or carboxylic ester and is represented by formula

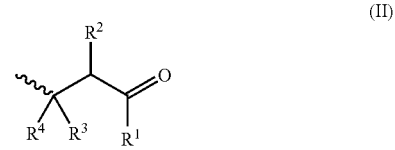

(II)

in which the wavy line indicates the location of the bond between said P and X;

$R^1$ represents a hydrogen atom, a $C_1$ to $C_6$ alkoxyl radical or a $C_1$ to $C_{15}$ linear, cyclic or branched alkyl, alkenyl or alkadienyl radical, possibly substituted by $C_1$ to $C_4$ alkyl groups; and $R^2$, $R^3$ and $R^4$ represent a hydrogen atom, a $C_6$ to $C_{10}$ aromatic ring or a $C_1$ to $C_{15}$ linear, cyclic or branched alkyl, alkenyl or alkadienyl radical, possibly substituted by $C_1$ to $C_4$ alkyl groups; or two, or three, of the groups $R^1$ to $R^4$ are bound together to form a saturated or unsaturated ring having 5 to 20 carbon atoms and, including the carbon atom to which said $R^1$, $R^2$, $R^3$ or $R^4$ groups are bound, this ring being possibly substituted by $C_1$ to $C_8$ linear, branched or cyclic alkyl or alkenyl groups;

X represents a functional group selected from the group consisting of the formulae i) to v):

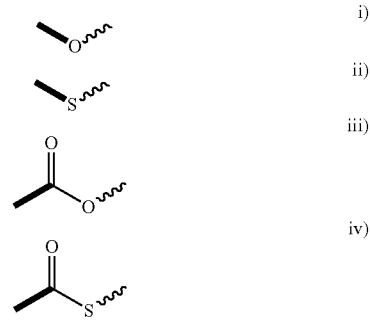

v)

in which formulae the wavy lines are as defined above and the bold lines indicate the location of the bond between said X and L, and $R^5$ represents a hydrogen atom or a $C_1$-$C_4$ alkyl group;

L represents a $C_2$-$C_{15}$ hydrocarbon group optionally comprising from 1 to 10 oxygen, sulfur or nitrogen atoms;

Z represents an oxygen or sulfur atom or a $NR^5$ group, $R^5$ representing a hydrogen atom or a $C_1$-$C_4$ alkyl group;

the $R^6$ groups represent independently of each other a hydrogen atom or a $C_1$-$C_4$ hydrocarbon group; and M represents a hydrogen atom, an alkali or earth alkali metal ion if Z represents an oxygen or sulfur atom or a hydrogen atom if Z represents a $NR^5$ group.

As "odoriferous α,β-unsaturated ketone, aldehyde or carboxylic ester", expression used in the definition of P, we mean here an α,β-unsaturated ketone, aldehyde or carboxylic ester which is recognized by a person skilled in the art as being used in perfumery as perfuming ingredient. In general, said odoriferous α,β-unsaturated ketone, aldehyde or carboxylic ester is a compound having from 8 to 20 carbon atoms, or even more, preferably between 10 and 15 carbon atoms.

According to a particular embodiment of formula (I), P represents a radical of the formulae (P-1) to (P-11), in the form of any one of its isomers:

(P-1)

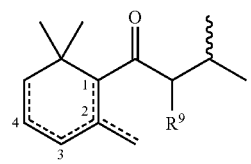

(P-2)

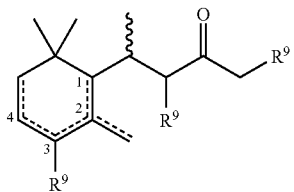

(P-3)

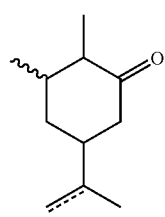

(P-4)

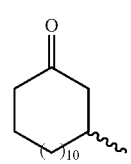

(P-5)

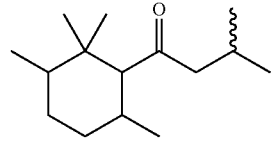

(P-6)

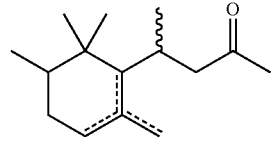

(P-7)

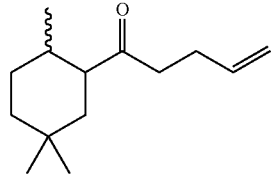

(P-8)

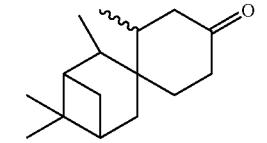

(P-9)

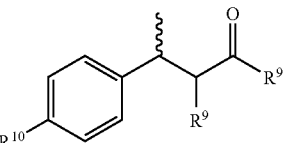

(P-10)

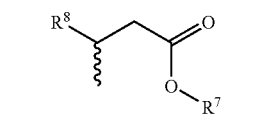

(P-11)

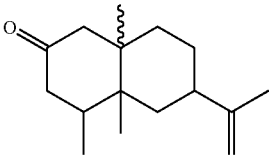

in which formulae the wavy lines have the meaning indicated above and the dotted lines represent a single or double bond, $R^7$ indicating a methyl or ethyl group, $R^8$ representing a $C_6$ to $C_9$ linear or branched alkyl, alkenyl or alkadienyl group, $R^9$ being a hydrogen atom or a methyl group and $R^{10}$ representing a hydrogen atom, a hydroxy or methoxy group or a $C_1$-$C_4$ linear or branched alkyl group.

In particular P may also represent a radical of the formula (P-1) or (P-7) as defined above. Even more particularly P may represent a compound of formula (P-1).

According to another embodiment of the invention, X represents a functional group selected from the group consisting of the formulae i) to iii)

i)

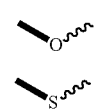

ii)

-continued

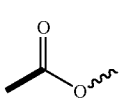
iii)

as defined above. More specifically X may represent an oxygen or a sulfur atom.

According to another embodiment of the invention, Z represents an oxygen atom or a $NR^5$ group, $R^5$ representing a hydrogen atom or a methyl group. Alternatively, Z may represent an oxygen atom.

According to another embodiment of the invention one $R^6$ represents a hydrogen atom and the other a methyl group or a hydrogen atom. Alternatively, both $R^6$ represent a hydrogen atom.

According to another embodiment of the invention, L represents a $C_2$-$C_{12}$ hydrocarbon group optionally comprising from 1 to 7 oxygen, sulfur or nitrogen atoms. Alternatively, L may represent a $C_2$-$C_{10}$ hydrocarbon group optionally comprising from 1 to 7 oxygen, sulfur or nitrogen atoms. Specific, but not limiting examples of such group L are the one of the formulae (a) to (d):

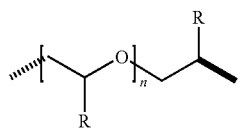
(a)

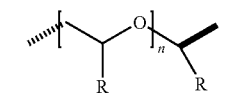
(b)

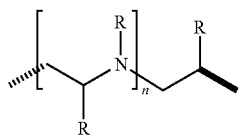
(c)

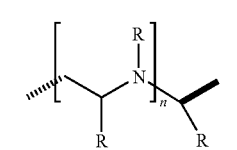
(d)

wherein the hatched line indicates the location of the bond between said L and Z and the bold line the connection between L and X; n represents an integer from 1 to 5 and R a hydrogen atom or a methyl or ethyl group. In particular the group L of formula (b) or (d) can be used when X is a group of formula iii) or iv), while the group L of formula (a) or (c) can be used when X is a group of formula i), ii) or v).

Alternatively, L may represent also a linear or branched $C_2$-$C_5$ alkyl group, and in particular $C_2$, $C_3$ or $C_4$ linear or branched alkyl groups.

The invention's co-polymers may be in the form of a random co-polymer or of a block co-polymer. According to a particular embodiment of the invention, the co-polymer is preferentially of the random, or statistic, type.

Furthermore, according to another embodiment of the invention, the invention's co-polymer may be characterized by a molecular weight comprised in the range between 500 Da and 1000000 Da, more particularly between 2000 Da and 200000 Da.

Furthermore, it is also useful to mention that the molar ratio between the total amount of the repeating unit (I) and the total amount of repeating units of the invention's co-polymers (hereinafter (I)/(Tot)) can be comprised between 1/100 and 100/100, and in particular between 5/100 and 100/100, or even between 20/100 and 95/100.

The invention's co-polymers comprise at least one other repeating unit and may be optionally cross-linked. Said other repeating units can be of the formula

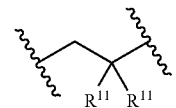
(III)

wherein the $R^{11}$ groups represent independently of each other
  a hydrogen or halide atom;
  a $C_1$-$C_6$ hydrocarbon group optionally comprising from 1 to 4 heteroatoms selected from the group consisting of oxygen and sulfur atoms;
  a carboxylic group of formula $COOR^{12}$ wherein $R^{12}$ represents a hydrogen atom, a $C_1$-$C_{60}$ alkyl or alkenyl group optionally comprising from 1 to 30 oxygen atoms;
  a $OR^{13}$ group, wherein $R^{13}$ represents a hydrogen atom, a $C_1$-$C_6$ alkyl group or a $COR^{14}$ group, $R^{14}$ representing a $C_1$-$C_6$ alkyl group; or
  a pyrrolidone unit, connected by the nitrogen atom.

According to a particular embodiment of the invention one of the $R^{11}$ groups represents a hydrogen atom. According to a particular embodiment of the invention the $R^{12}$ group represents a hydrogen atom, a $C_1$-$C_{25}$ alkyl or alkenyl group optionally comprising from 1 to 14 oxygen atoms.

According to a particular embodiment of the invention the $R^{11}$ groups represent independently of each other
  a hydrogen or halide atom;
  a $C_1$-$C_6$ hydrocarbon group optionally comprising from 1 to 2 heteroatoms selected from the group consisting of oxygen and sulfur atoms;
  a carboxylic group of formula $COOR^{12}$ wherein $R^{12}$ represents a hydrogen atom, a $C_1$-$C_{10}$ alkyl or alkenyl group optionally comprising from 1 to 5 oxygen atoms;
  a $OR^{13}$ group, wherein $R^{13}$ represents a hydrogen atom, a $C_1$-$C_2$ alkyl group or a $COR^{14}$ group, $R^{14}$ representing a $C_1$-$C_3$ alkyl group; or
  a pyrrolidone unit, connected by the nitrogen atom.

Another type of said other repeating units can be of the formula

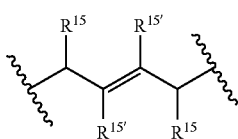
(IV)

wherein the groups $R^{15}$ or $R^{15'}$ represent a hydrogen atom or methyl or ethyl group, the two $R^{15}$ can be bonded together and represent an oxygen atom or a $CH_2O$ group.

The invention's co-polymer may be synthesized from commercially available compounds by conventional methods, such as the one mentioned hereinbelow.

According to any one of the above-mentioned embodiments, a particular type of co-polymers of the invention, hereinafter named compounds (V), are the ones obtainable by a process comprising the following steps A) reacting together:
a co-polymer obtainable by reacting together at least one olefin of formula $CH_2=CR^{11}_2$, $R^{11}$ being as defined above for the unit (III), and at least a derivative of formula

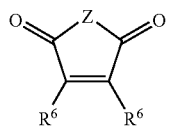

(VI)

wherein the $R^6$ groups and Z have the same meaning as indicated above; and
a compound of formula P-X-L-Z-M, wherein P, X, L, Z and M have the same meaning indicated above;

B) optionally hydrolyze all or part of the unreacted anhydride functional group of the polymerized monomer (VI) of the co-polymer; and/or C) optionally react the co-polymer obtained in step A) or B) with a base.

According to an embodiment of the invention said olefin $CH_2=CR^{11}_2$ is of formula $CH_2=CHR^{11}$, and $R^{11}$ has the meaning provided above.

Non limiting examples of such olefins are 1-alkenes such as 1-octadecene, styrene, (meth)acrylic acid, vinyl acetate/alcohol, sulfonated styrene, ethylene, isobutylene or diisobutylene, methoxyethylene, polyoxyethylene (2-methyl-2-propenyl)methyl diether, vinylether or divinylether (DIVEMA, MVE 2, MVE 5, MVE-2, MVE-5, NSC 46015, NSC-46015, NSC46015, pyran copolymer, see for example U.S. Pat. No. 4,010,254), vinylchloride, stearyl (meth)acrylate or lauryl (meth)acrylate, 2-hydroxyethyl (meth)acrylate, alkyl (meth)acrylate, ethylene glycol methyl ether (meth)acrylate, poly(ethylene glycol) (meth)acrylate, poly(ethylene glycol) methyl ether (meth)acrylate, N,N-dimethylaminoethyl (meth)acrylate and its quaternized form, difurylmethane, vinylpyrrolidone, butadiene, or 2-ethoxyethylmethacrylate.

The chemical structure of the co-polymer used in step A) comprises the following repeating units (VII) and (VIII):

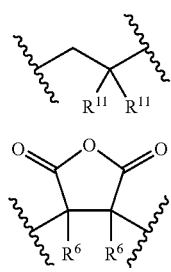

(VII)

(VIII)

wherein $R^{11}$ and $R^6$ have the meaning indicated above.

So the co-polymer used in step A) can be characterized also by a molar ratio (VII)/(VIII) comprised between 99/1 and 60/40, or comprised between 90/10 and 60/40, or even between 70/30 and 55/45.

Step A) of the above-described process implies the reaction of the repeating unit (VIII) of the co-polymer (V) with a compound of formula P-X-L-Z-M, said compound can be added in a molar ratio comprised between 1/100 and 100/100, relative to the total amount of repeating unit (VIII) present in the co-polymer (V). As a consequence of such reaction the chemical structure of the compound (V) comprises the repeating units (IX)

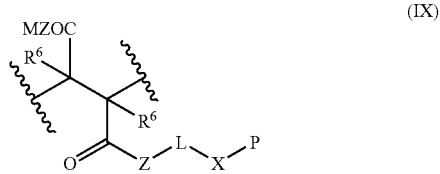

(IX)

wherein M, $R^6$, Z, L, X and P have the meaning indicated above.

Step B) of the above-described process implies the hydrolysis of the unreacted repeating unit (VIII) of the co-polymer (V) with a hydrolyzing agent, which can be a base or an acid. Step C) of the above-described process implies the reaction of the hydrolyzed repeating unit (VIII) with a base. In general, as hydrolyzing agent and/or base can be used an alkali metal hydroxide or an alkali-earth metal hydroxide. Said hydrolyzing agent and/or base ban be reacted in a molar amount comprised between 1/100 and 1/1, relative to the total amount of [repeating unit (VIII)–repeating unit (IX)]. Specific examples of hydroxides are NaOH or KOH. As previously mentioned the hydrolysis can be performed also with an acid, and said acid can be any conventional acid generally used to hydrolyze an anhydride group. As hydrolyzing agent can also used the medium of the consumer product into which the invention's co-polymer is added.

Alternatively, all or part of the unreacted repeating unit (VIII) of the co-polymer (V) can be hydrolyzed with an alcohol of formula $R^xOH$, wherein $R^x$ represents a $C_1$-$C_4$ alkyl group, preferably methyl or ethyl, or a polyether having a molecular weight comprised between 100 and 4000 g/mol, preferably between 200 and 1000 g/mol. According to a particular embodiment, alcohol $R^xOH$ can be a polyethylene glycol.

Consequently, the chemical structure of the compound (V) can optionally comprise also the repeating unit (X) or (X')

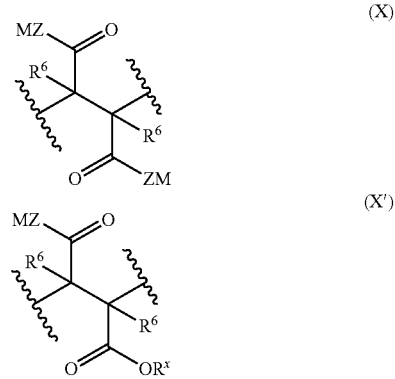

(X)

(X')

wherein M, Z, $R^x$ and $R^6$ have the meaning indicated above.

So compounds (V) can be characterized also by a molar ratio (VIII)/[(IX)+(X)+(X')] comprised between 0/100 and 95/5, or comprised between 2/98 and 70/30.

Said co-polymers (V) may also comprise other co-monomers and be optionally cross-linked. For examples such other co-monomers may represent up to 10% of the total amount of repeating unit. Non-limiting examples of such other co-monomers are the compounds of formula (XI)

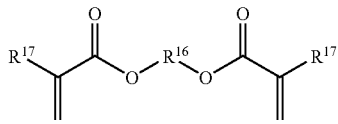

wherein $R^{17}$ represents a hydrogen atom or a methyl group and $R^{16}$ represents a $C_2$-$C_8$ alkanediyl group or a —[$CH_2CHR^{17}O$]$_m$$CH_2CHR^{17}$— group, m representing an integer from 0 to 10 and $R^{17}$ has the meaning indicated above.

Specific, but non-limiting, examples of said co-polymers, and which are commercially available, are the following: styrene-maleic anhydride copolymer, (meth)acrylic acid-maleic anhydride copolymer, vinyl acetate/alcohol-maleic anhydride copolymer, sulfonated styrene-maleic anhydride copolymer, ethylene-maleic anhydride copolymer, isobutylene or diisobutylene-maleic anhydride copolymer, methylvinylether-maleic anhydride copolymer (as for example those commercialized under the trade name Gantrez®), polyoxyethylene (2-methyl-2-proprenyl)methyl diether-maleic anhydride copolymer, vinylether or divinylether-maleic anhydride copolymer (DIVEMA, MVE 2, MVE 5, MVE-2, MVE-5, NSC 46015, NSC-46015, NSC46015, Pyran Copolymer) (see for example U.S. Pat. No. 4,010,254), vinylchloride-maleic anhydride copolymer, stearyl methacrylate-maleic anhydride copolymer, lauryl methacrylate-maleic anhydride copolymer, difurylmethane-maleic anhydride copolymer, vinylpyrrolidone-maleic anhydride copolymer, butadiene-maleic anhydride copolymer, 2-ethoxyethylmethacrylate-styrene-maleic anhydride copolymer.

According to a particular embodiment of compounds (V), said co-polymers are those wherein P is as defined hereinabove;
X represents a sulfur atom;
L represents a linear, branched or cyclic saturated or unsaturated $C_2$-$C_6$ group;
M represents a sodium, potassium, calcium, magnesium or hydrogen atom;
Z represents an oxygen atom; and
the copolymer is one obtained by the co-polymerisation of maleic anhydride and an olefin selected from the group consisting of 1-octadecene, ethylene, isobutylene or methoxyethylene.

In said embodiment, if applicable, $R^x$ can be as define d above.

The compounds of formula P-X-L-Z-M are obtainable by the [1,4]-addition reaction between an odoriferous α,β-unsaturated ketone, aldehyde or carboxylic ester of formula (P')

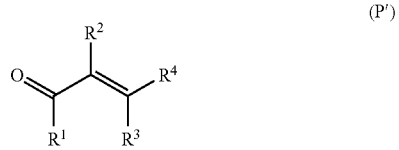

wherein the configuration of the carbon-carbon double bond can be of the (E) or (Z) type and the symbols $R^1$, $R^2$, $R^3$ and $R^4$ have the meaning indicated in formula (II); and an appropriate compound of formula M-X-L-Z-M, wherein all the symbols have the meaning given in formula (I). For practical reasons, and according to the nature and nucleophilicity of the functional group X, the invention's compounds may be more advantageously obtained by the reaction between the compound of formula (P'''), which is the aldol derivative of the odoriferous compound of formula (P'),

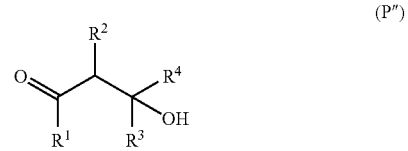

wherein the symbols $R^1$, $R^2$, $R^3$ and $R^4$ have the meaning indicated in formula (II); and an appropriate compound (well known by a person skilled in the art) providing the moiety L-Z-M or an equivalent thereof, such as for example a lactone.

The use of the aldol derivative is particularly interesting for the synthesis of all the compounds of formula (I) wherein X represents, e.g., an oxygen atom or a carboxylic group. On the other hand, the direct use of the odoriferous molecule as starting material is particularly interesting for the synthesis of all the compounds of formula (I) wherein X represents, e.g., a sulfur atom.

Owing to their particular chemical structure the invention's polymers or co-polymers are capable of releasing, via a decomposition reaction, a residue and an odoriferous molecule such as, for example, an α,β-unsaturated ketone, aldehyde or carboxylic ester of formula (P').

It is not possible to provide an exhaustive list of compounds of formula (P'), which can be used in the synthesis of the compound (I) and subsequently be released. However, the following can be named as preferred examples: 2-alkenyl-2-cyclopenten-1-one, 2-alkyl-2-cyclopenten-1-one, 2-cyclopentadecen-1-one, 6,6-dimethyl-bicyclo[3.1.1]hept-2-ene-2-carbaldehyde, 1-(3,3 or 5,5-dimethyl-1-cyclohexen-1-yl)-1-ethanone, 1-(5,5-dimethyl-1-cyclohexen-1-yl)-4-penten-1-one, (E)-1-(2,2-dimethyl-6-methylene-1-cyclohexyl)-2-buten-1-one (γ-damascone), (E)-4-(2,2-dimethyl-6-methylene-1-cyclohexyl)-3-buten-2-one (γ-ionone), 2,5-dimethyl-5-phenyl-1-hexen-3-one, ethyl 2,4-decadienoate, ethyl 2-octenoate, ethyl 2,4-undecadienoate, 4,4A,5,6,7,8-hexahydro-6-isopropenyl-4,4A-dimethyl-2(3H)-naphthalenone (Nootkatone), 2-hexenal, (E)-2-hexyl-3-phenyl-2-propenal, 4-isopropyl-2-cyclohexen-1-one, 4-(4-hydroxyphenyl)-3-buten-2-one, 5-isopropyl-2-methyl-2-cyclohexen-1-one (1(6)-p-menthen-2-one), 1,8-p-menthadien-7-al, 1(6),8-p-menthadien-2-one, 1-p-menthen-7-al, 1-(4-methoxy-1-phenyl)-1-penten-3-one, methyl 5,9-dimethyl-2,4,8-decatrienoate, 5-methyl-2-hepten-4-one, methyl 2-nonenoate, methyl 2-octenoate, 3-methyl-5-propyl-2-cyclohexen-1-one, (E)-3-methyl-4-(2,6,6-trimethyl-2-cyclohexen-1-yl)-3-buten-2-one, 2,6-nonadienal, 2-nonenal, 2-octenal, (E)-3-phenyl-2-propenal (cinnamic aldehyde), (E)-4-(2,5,6,6-tetramethyl-1-cyclohexen-1-yl)-3-buten-2-one, (E)-4-(2,5,6,6-tetramethyl-2-cyclohexen-1-yl)-3-buten-2-one, 1-(2,2,3,6-tetramethyl-1-cyclohexyl)-2-buten-1-one, 4-(2,2,3,6-tetramethyl-1-cyclohexyl)-3-buten-2-one, 2,6,6-trimethyl-bicyclo [3.1.1] heptane-3-spiro-2'-cyclohexen-4'-one, (E)-1-(2,6,6-trimethyl-1,3-cyclohexadien-1-yl)-2-buten-1-one (β-damascenone), (E)-1-(2,6,6-trimethyl-1-cyclohexen-1-yl)-2-buten-1-one (β-damascone), (E)-1-(2,6,6-trimethyl-2-cyclohexen-1-yl)-2-buten-1-one (α-damascone), (E)-1-(2,6,6-trimethyl-3-cyclohexen-1-yl)-

2-buten-1-one (δ-damascone), (E)-4-(2,6,6-trimethyl-1-cyclohexen-1-yl)-3-buten-2-one (β-ionone), (E)-4-(2,6,6-trimethyl-2-cyclohexen-1-yl)-3-buten-2-one (α-ionone), (E)-1-(2,6,6-trimethyl-1-cyclohexen-1-yl)-1-penten-3-one and (E)-1-(2,6,6-trimethyl-2-cyclohexen-1-yl)-1-penten-3-one. Of course, the aldol derivatives of formula (P''') of the latter compounds are also useful in the synthesis of the invention's compounds.

According to a particular embodiment of the invention the following compounds of formula (P') can be cited: 2-cyclopentadecen-1-one, 1-(5,5-dimethyl-1-cyclohexen-1-yl)-4-penten-1-one, (E)-1-(2,2-dimethyl-6-methylene-1-cyclohexyl)-2-buten-1-one (γ-damascone), (E)-4-(2,2-dimethyl-6-methylene-1-cyclohexyl)-3-buten-2-one (γ-ionone), 2,5-dimethyl-5-phenyl-1-hexen-3-one, ethyl 2,4-decadienoate, ethyl 2-octenoate, ethyl 2,4-undecadienoate, 4,4A,5,6,7,8-hexahydro-6-isopropenyl-4,4A-dimethyl-2(3H)-naphthalenone (Nootkatone), 1(6),8-p-menthadien-2-one, methyl 5,9-dimethyl-2,4,8-decatrienoate, methyl 2-nonenoate, methyl 2-octenoate, 3-methyl-5-propyl-2-cyclohexen-1-one, 2-octenal, (E)-3-phenyl-2-propenal (cinnamic aldehyde), 1-(2,2,3,6-tetramethyl-1-cyclohexyl)-2-buten-1-one, 4-(2,2,3,6-tetramethyl-1-cyclohexyl)-3-buten-2-one, 2,6,6-trimethyl-bicyclo[3.1.1]heptane-3-spiro-2'-cyclohexen-4'-one, (E)-1-(2,6,6-trimethyl-1,3-cyclohexadien-1-yl)-2-buten-1-one (β-damascenone), (E)-1-(2,6,6-trimethyl-1-cyclohexen-1-yl)-2-buten-1-one (β-damascone), (E)-1-(2,6,6-trimethyl-2-cyclohexen-1-yl)-2-buten-1-one (α-damascone), (E)-1-(2,6,6-trimethyl-3-cyclohexen-1-yl)-2-buten-1-one (δ-damascone), (E)-4-(2,6,6-trimethyl-1-cyclohexen-1-yl)-3-buten-2-one (β-ionone) and (E)-4-(2,6,6-trimethyl-2-cyclohexen-1-yl)-3-buten-2-one (α-ionone).

Amongst the odoriferous compounds cited in the lists hereinabove, the preferred ones are: β-damascenone, damascones, ionones, 2-cyclopentadecen-1-one, 1-(5,5-dimethyl-1-cyclohexen-1-yl)-4-penten-1-one, 1(6),8-p-menthadien-2-one, 1-(2,2,3,6-tetramethyl-1-cyclohexyl)-2-buten-1-one and 4-(2,2,3,6-tetramethyl-1-cyclohexyl)-3-buten-2-one.

Therefore, the invention's compounds capable of releasing such compounds (P') are also a particularly appreciated embodiment of the invention.

An example of the above-mentioned decomposition reaction is illustrated in the following scheme, wherein only one unit is shown:

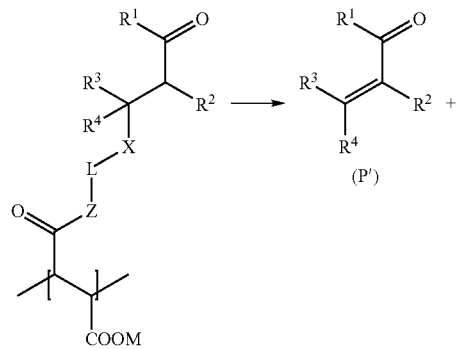

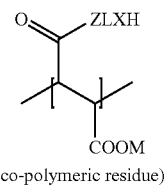

(co-polymeric residue)

The decomposition reaction, which leads to the release of the odoriferous molecules, is believed to be influenced by pH changes or by heat, but may also be triggered by other types of mechanisms.

As mentioned above, the invention concerns the use of the above-described co-polymers as perfuming ingredients. In other words it concerns a method to confer, enhance, improve or modify the odor properties of a perfuming composition or of a perfumed article, which method comprises adding to said composition or article an effective amount of at least a co-polymer according to the invention. By "use of an invention's co-polymer" it has to be understood here also the use of any composition containing said co-polymer and which can be advantageously employed in perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one invention's co-polymer as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

Generally speaking, by "perfumery base" we mean here a composition comprising at least one perfuming co-ingredient.

Said perfuming co-ingredient is not a co-polymer according to the invention. Moreover, by "perfuming co-ingredient" it is meant here a compound, which is used in a perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one co-polymer and at least one perfumery carrier represents a particular embodiment of the invention as well as a perfuming composition comprising at least one co-polymer, at least one perfumery carrier, at least one perfuming base, and optionally at least one perfumery adjuvant.

It is useful to mention here that the possibility to have, in the compositions mentioned above, more than one of the invention's co-polymers is important as it enables the perfumer to prepare accords, perfumes, possessing the odor tonality of various compounds of the invention, creating thus new tools for their work.

Furthermore, an invention's co-polymer, or a perfuming composition comprising it, is a useful perfuming ingredient, which can be advantageously used in all the fields of modern perfumery, such as fine perfumery or functional perfumery. Indeed, the invention's compounds may be advantageously employed in fine or functional perfumery to achieve a more controlled deposition, and consequent release, of odoriferous compounds. For example, the co-polymers according to the invention, owing to a good substantivity, a low volatility and a well controlled release of odoriferous molecules, can be incorporated in any application requiring the effect of rapid or prolonged liberation of an odoriferous component as defined hereinabove and furthermore can impart a fragrance and a freshness to a treated surface which will last well beyond the rinsing and/or drying processes. Suitable surfaces are, in particular, textiles, hard surfaces, hair and skin.

Consequently, a perfumed article comprising:
i) as perfuming ingredient, at least one invention's co-polymer as defined above; and
ii) a consumer product base;
is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's polymer or co-polymer.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or anti-perspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

Preferred perfuming compositions or perfumed articles are perfumes, fabric detergents or softener bases.

Typical examples of fabric detergents or softener composition into which the compounds of the invention can be incorporated are described in WO 97/34986 or in U.S. Pat. Nos. 4,137,180 and 5,236,615 or EP 799 885. Other typical detergent and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The above-mentioned consumer product bases are all characterized by being practically neutral (e.g. body care products or perfumes), acidic (e.g. fabric softeners) or basic (e.g. detergents, soaps), while the copolymers of the invention can be either non-ionic or ionic (cationic or anionic).

We have found that, according to a particular embodiment of the invention, when the consumer product bases have a pH value below 6, (such as softeners) then it is preferable to combine such a base with an invention's copolymer having an increased negative charge at basic or neutral pH as compared to acidic pH, i.e. a copolymer comprising COOM groups.

The proportions in which the compounds according to the invention can be incorporated into the various aforementioned articles or compositions vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 20% by weight, or even more, of the invention's compound based on the weight of the composition into which they are incorporated. Concentrations lower than these, such as in the order of 0.001% to 5% by weight, can be used when this compound is applied directly in the perfuming of the various consumer products mentioned hereinabove.

Another object of the present invention relates to a method for the perfuming of a surface or to a method for intensifying or prolonging the diffusion effect of the characteristic fragrance of an odoriferous ingredient on a surface, characterized in that said surface is treated in the presence of an invention's compound. Suitable surfaces are, in particular, textiles, hard surfaces, hair and skin.

EXAMPLES

The invention will now be described in further detail by way of the following examples, wherein the abbreviations have the usual meaning in the art, the temperatures are indicated in degrees centigrade (° C.); the NMR spectral data were recorded in CDCl₃ (if not stated otherwise) on a Bruker DPX 400 spectrometer with 400 MHz for $^1$H and 100 MHz for $^{13}$C, the chemical displacements δ are indicated in ppm with respect to the TMS as standard, the coupling constants J are expressed in Hz.

Commercially available reagents and solvents were used without further purification, if not stated otherwise. IR Spectra: Perkin Elmer Spectrum One FTIR spectrometer, v in $cm^{-1}$. Analytical Size Exclusion Chromatography (SEC) analyses were performed at room temperature (ca. 22° C.) on a ThermoFinnigan Surveyor system composed of a vacuum online degasser, quaternary LC pump, autosampler and UV/Vis detector combined with a ThermoSeparationProducts (tsp) Spectra System IR-150 refractometer and a Viscotek 270 Dual Detector viscometer. Samples were eluted from a Macherey-Nagel Nucleogel GPC 104-5 column (300× 7.7 mm i.d., particle size 5 μm) at a flow rate of 1.0 ml/min using HPLC grade THF from SDS. Universal calibrations were carried out with the viscometer and the RI detector using commercial poly(methyl methacrylate) (PMMA) polymer standards from Fluka. About 40 mg of the polymer standards were precisely weighed and dissolved in 10 ml of solvent, then 50 μl of these solutions were injected for the calibration.

The following starting polymeric materials are alternated copolymers of various olefinic monomers and maleic anhydride, meaning a ratio of 50% between the two different repetitive units.

In the synthesis of the invention's co-polymers, by "conversion" it is meant the amount, in percentage, of the repeating unit (VIII) converted into the repeating unit (IX).

Example 1

Preparation of poly(1-octadecene-alt-maleic acid mono-{2-[1-methyl-3-oxo-3-(2,6,6-trimethyl-cyclohex-3-enyl)-propylsulfanyl]-ethyl}ester)

a) Preparation of 3-(2-hydroxy-ethylsulfanyl)-1-(2,6,6-trimethyl-cyclohex-3-enyl)-butan-1-one: 2-Mercaptoethanol (origin: Aldrich, 3.5 ml, 50 mmol) in 20 ml of THF was added dropwise at 45° C. to a solution of (E)-1-(2,6,6-trimethyl-3-cyclohexen-1-yl)-2-buten-1-one (δ-damascone, 52.1 mmol) and 1,8-diazabicyclo[5.4.0]undec-7-ene (1, 5-5) (DBU, 0.78 ml, 5.21 mmol) in 50 ml of THF. The reaction medium was stirred for 12 h and then treated with an aqueous solution of HCl (5%). The aqueous phase was extracted with Et₂O and joined to the organic phase which has been washed with a saturated solution of NaHCO₃ and then with a saturated solution of NaCl. The organic phase was dried over Na₂SO₄, filtered and concentrated. The product was obtained as colorless oil.

$^1$H-NMR: 5.53 (m, 1H); 5.45 (m, 1H); 3.77 (m, 2H); 3.35 (sext, 1H); 2.96 (m, 1H); 2.88 (m, 1H); 2.86-2.63 (m, 4H); 2.60-2.45 (m, 1H); 2.23 (m, 1H); 1.97 (m, 1H); 1.70 (m, 1H); 1.31 (m, 3H); 1.02 (m, 1H); 0.96 (m, 5H); 0.92 (d, 2H); 0.88 (d, 1H);

$^{13}$C-NMR: 212.76s; 212.61s, 131.81d; 131.68d; 124.23d; 124.13d; 67.96t; 62.89d; 61.15t; 61.13t; 55.13t; 41.75t; 41.70t; 36.48q; 34.38t; 34.27t; 34.05d; 33.98d; 33.20q; 33.13q; 31.75d; 31.69d; 31.44d; 31.38d; 29.85q; 29.75q; 25.60t; 22.32q; 22.14q; 20.75q; 20.73q; 19.92q; 19.88q;

IR: 3415w-3018w-2956m-2928m-2871m-2830w-1703s-1667m-1625m-1457m-1430w-1386m-1366s-1286w-1250w-1212w-1153m-1115m-1044s-999s-953w-932w-895w-843w-690s.

b) Preparation of poly(1-octadecene-alt-maleic acid mono-{2-[1-methyl-3-oxo-3-(2,6,6-trimethyl-cyclohex-3-enyl)-propylsulfanyl]-ethyl}ester): poly(1-octadecene-alt-maleic anhydride) (origin: Aldrich, 5 mmol) was dissolved in 30 ml of THF. A solution of 3-(2-hydroxy-ethylsulfanyl)-1-(2,6,6-trimethyl-cyclohex-3-enyl)-butan-1-one (5 mmol) in 10 ml of THF was added dropwise. Then, a solution of triethylamine (5 mmol) and N,N-dimethylaminopyridine (DMAP, 30.50 mg, 0.25 mmol, 5-mol %) in 20 ml of THF was added dropwise. The medium was heated at 70° C. for 48 h. The polymer solution was diluted with methylene chloride and extracted with an aqueous solution of HCl (5%), dried over Na₂SO₄, filtered, concentrated and precipitated into heptane. The product has been obtained as a white solid (m=0.70 g). Yield=23% with a conversion of 28%.

$^1$H-NMR: 5.52 (m, 1H); 5.46 (m, 1H); 4.21 (m, 2H); 3.78 (m, 1H); 3.37 (m, 3H); 2.96 (s, 3H); 2.89 (s, 3H); 2.85 (s, 1H); 2.73 (m, 4H); 2.51 (m, 1H); 2.38 (m, 1H); 2.21 (m, 2H); 2.00 (m, 4H); 1.69 (m, 4H); 1.26 (m, 78H); 0.96 (m, 6H); 0.87 (m, 12H);

$^{13}$C-NMR: 162.64s; 131.85d; 124.14d; 62.97d; 61.12t; 55.17t; 49.49t; 41.79t; 36.51q; 34.36t; 34.10t; 33.19t; 31.97t; 31.79d; 31.48q; 30.69t; 29.81t; 29.62t; 29.41t; 22.71t; 22.36q; 22.18q; 20.76q; 19.94q; 19.90q; 17.69q; 14.12q;

IR: 3783 to 2190m-3019w-2921s-2852s-1781w-1720m-1708m-1649m-1550m-1456m-1404m-1387m-1299w-1171m-1114w-1069w-998w-932w-841w-796w-719m-690m-666m.

$M_w$ (SEC)=108000 Da.

Example 2

Preparation of poly(isobutylene-alt-maleic acid mono-{2-[1-methyl-3-oxo-3-(2,6,6-trimethyl-cyclohex-3-enyl)-propylsulfanyl]-ethyl}ester)

Poly(isobutylene-alt-maleic anhydride) (origin: Aldrich, 5 mmol) was dissolved in 30 ml of N-methylpyrrolidinone (NMP). A solution of 3-(2-hydroxy-ethylsulfanyl)-1-(2,6,6-trimethyl-cyclohex-3-enyl)-butan-1-one (5 mmol, prepared as described in Example 1a) in 10 ml of NMP was added dropwise. Then, a solution of triethylamine (5 mmol) and DMAP (30.50 mg, 0.25 mmol, 5-mol %) in 20 ml of NMP was added dropwise. The medium was heated at 70° C. for 48 h. The polymer solution was diluted with methylene chloride and extracted with an aqueous solution of HCl (5%), dried over Na₂SO₄, filtered, concentrated and precipitated into heptane. The product has been obtained as a white solid (m=1.20 g). Yield=57% with a conversion of 8%.

IR: 3771 to 2150m-2969m-2882m-1850w-1776s-1734s-1718s-1637s-1472m-1449m-1399m-1375m-1301m-1171s-1063s-980s-912s-831w-792w-661w.

$M_w$ (SEC)=91000 Da.

Example 3

Preparation of poly(ethylene-alt-maleic acid mono-{2-[1-methyl-3-oxo-3-(2,6,6-trimethyl-cyclohex-3-enyl)-propylsulfanyl]-ethyl}ester)

Poly(ethylene-alt-maleic anhydride) (origin: Aldrich, 5 mmol) was dissolved in 30 ml of THF. A solution of 3-(2-hydroxy-ethylsulfanyl)-1-(2,6,6-trimethyl-cyclohex-3-enyl)-butan-1-one (5 mmol, prepared as described in Example 1a) in 10 ml of THF was added dropwise. Then, a solution of triethylamine (5 mmol) and DMAP (30.50 mg, 0.25 mmol, 5-mol %) in 20 ml of THF was added dropwise. The medium was heated at 70° C. for 48 h. The polymer solution was diluted with methylene chloride and extracted with an aqueous solution of HCl (5%), dried over $Na_2SO_4$, filtered, concentrated and precipitated into heptane. The product has been obtained as a white solid (m=1 g). Yield=50% with a conversion of 91%.

IR: 3750 to 2150m-3017w-2956m-2934m-2872m-1779w-1722s-1703s-1698s-1652m-1506w-1453m-1391m-1367m-1153s-999w-936w-896w-761m-691w-673w-611w.

Example 4

Preparation of poly(methoxyethylene-alt-maleic acid mono-{2-[1-methyl-3-oxo-3-(2,6,6-trimethyl-cyclohex-3-enyl)-propylsulfanyl]-ethyl}ester)

Poly(methoxyethylene-alt-maleic anhydride (Gantrez® AN-119 BF, origin: ISP Technologies, 5 mmol) was dissolved in 30 ml of THF. A solution of 3-(2-hydroxy-ethylsulfanyl)-1-(2,6,6-trimethyl-cyclohex-3-enyl)-butan-1-one (5 mmol, prepared as described in Example 1a) in 10 ml of THF was added dropwise. Then, a solution of triethylamine (5 mmol) and DMAP (30.50 mg, 0.25 mmol, 5-mol %) in 20 ml of THF was added dropwise. The medium was heated at 70° C. for 48 h. The polymer solution was diluted with methylene chloride and extracted with an aqueous solution of HCl (5%), dried over $Na_2SO_4$, filtered, concentrated and precipitated into heptane. The product has been obtained as a solid (m=1 g). Yield=47% with a conversion of 80%.

$^1$H-NMR (MeOD): 5.54 (m, 1H); 5.46 (m, 1H); 4.22 (m, 2.4H); 3.67 (m, 3H); 3.36 (m, 9H); 2.96 (s, 5H); 2.81 (m, 3H); 2.66 (m, 1H); 2.47 (m, 2H); 2.32 (m, 1H); 2.02 (m, 3H); 1.69 (m, 2H); 1.38-1.22 (m, 7H); 1.01 (m, 3H); 0.92 (m, 7H);

$^{13}$C-NMR (MeOD): 175.5s; 132.92d; 125.50d; 78.50d; 63.85d; 58.20s; 56.10t; 47.99t; 42.60t; 35.80d; 34.16d; 33.06d; 30.17q; 23.75t; 22.40q; 21.70q; 20.60q; 14.45q; 9.30q;

IR: 3750 to 2323m-3011w-2954m-2934m-2903w-2832w-1779m-1727s-1705s-1650m-1455m-1441m-1387m-1367m-1165s-1088s-998s-924w-836w-798w-751w-690w.

$M_w$ (SEC)=98000 Da.

Example 5

Preparation of poly(methoxyethylene-alt-maleic acid mono-{2-[1-methyl-3-oxo-3-(2,6,6-trimethyl-cyclohex-2-enyl)-propylsulfanyl]-ethyl}ester)

a) Preparation of 3-(2-hydroxy-ethylsulfanyl)-1-(2,6,6-trimethyl-cyclohex-2-enyl)-butan-1-one: 2-Mercaptoethanol (3.5 ml, 50 mmol) in 20 ml of THF was added dropwise at 45° C. to a solution of (E)-1-(2,6,6-trimethyl-2-cyclohexen-1-yl)-2-buten-1-one (α-damascone, 52.1 mmol) and DBU (0.78 ml, 5.21 mmol) in 50 ml of THF. The reaction medium was stirred for 12 h and then treated with an aqueous solution of HCl (5%). The aqueous phase was extracted with $Et_2O$ and joined to the organic phase which has been washed with a saturated solution of $NaHCO_3$ and then with a saturated solution of NaCl. The organic phase was dried over $Na_2SO_4$, filtered and concentrated. The product was obtained as colorless oil (m=13.7 g). Yield=98%.

IR: 3418m-3030w-2959s-2919s-2870m-1707s-1670w-1623w-1448m-1400m-1386m-1364m-1347m-1315w-1259w-1223w-1176w-1139w-1131w-1048s-1012s-967w-934w-887m-811m-738w-647w-631w.

b) Preparation of poly(methoxyethylene-alt-maleic acid mono-{2-[1-methyl-3-oxo-3-(2,6,6-trimethyl-cyclohex-2-enyl)-propylsulfanyl]-ethyl}ester): Poly(methoxyethylene-alt-maleic anhydride (Gantrez® AN-119 BF, 5 mmol) was dissolved in 30 ml of THF. A solution of 3-(2-hydroxyethylsulfanyl)-1-(2,6,6-trimethyl-cyclohex-2-enyl)-butan-1-one (5 mmol) in 10 ml of solvent was added dropwise. Then, a solution of triethylamine (5 mmol) and DMAP (30.50 mg, 0.25 mmol, 5-mol %) in 20 ml of THF was added dropwise. The medium was heated at 70° C. for 48 h. The polymer solution was diluted with methylene chloride and extracted with an aqueous solution of HCl (5%), dried over $Na_2SO_4$, filtered, concentrated and precipitated into heptane. The product has been obtained as a solid (m=1 g). Yield=47% with a conversion of 88%.

IR: 3782 to 2166w-2933m-2836w-1779m-1767m-1723s-1717s-1708s-1666m-1648m-1578m-1438m-1385m-1363m-1164s-1083s-995m-923m-835w-658w.

$M_w$ (SEC)=26700 Da.

Example 6

Preparation of poly(methoxyethylene and maleic acid mono-{2-[1-methyl-3-oxo-3-(2,6,6-trimethyl-cyclohexa-2,4-dienyl)-propylsulfanyl]-ethyl}ester)

a) Preparation of 3-(2-hydroxy-ethylsulfanyl)-1-(2,6,6-trimethyl-cyclohexa-1,3-dienyl)-butan-1-one: 2-Mercaptoethanol (3.5 ml, 50 mmol) in 20 ml of THF was added dropwise at 45° C. to a solution of (E)-1-(2,6,6-trimethyl-1,3-cyclohexadien-1-yl)-2-buten-1-one (damascenone, 52.1 mmol) and DBU (0.78 ml, 5.21 mmol) in 50 ml of THF. The reaction medium was stirred for 12 h and then treated with an aqueous solution of HCl (5%). The aqueous phase was extracted with $Et_2O$ and joined to the organic phase which has been washed with a saturated solution of $NaHCO_3$ and then with a saturated solution of NaCl. The organic phase was dried over $Na_2SO_4$, filtered and concentrated. The product was obtained as colorless oil (m=13.4 g). Yield=47% with a conversion of 95%.

IR: 3434m-3036w-2958m-2921m-2869m-2813w-1683s-1645m-1585w-1462m-1450m-1420w-1397m-1379m-1358m-1345m-1288m-1172m-1149m-1122w-1044s-1001s-971w-933w-731s.

b) Preparation of poly(methoxyethylene and maleic acid mono-{2-[1-methyl-3-oxo-3-(2,6,6-trimethyl-cyclohexa-2,4-dienyl)-propylsulfanyl]-ethyl}ester): Poly(methoxyethylene-alt-maleic anhydride so-called Gantrez® AN-119 BF, 5 mmol) was dissolved in 30 ml of THF. A solution of 3-(2-hydroxy-ethylsulfanyl)-1-(2,6,6-trimethyl-cyclohexa-1,3-dienyl)-butan-1-one (5 mmol) in 10 ml of solvent was added dropwise. Then, a solution of triethylamine (5 mmol) and DMAP (30.50 mg, 0.25 mmol, 5-mol %) in 20 ml of THF was added dropwise. The medium was heated at 70° C. for 48 h. The polymer solution was diluted with methylene chloride and extracted with an aqueous solution of HCl (5%), dried over $Na_2SO_4$, filtered, concentrated and precipitated into heptane. The product has been obtained as a solid (m=1 g). Yield=47%.

IR: 3773 to 2162m-3032w-2934m-2832w-1780m-1722s-1711s-1651s-1565m-1508m-1439s-1385s-1359m-1210s-1170s-1084s-999w-972w-924w-834w-793w-771w-737w-662m.

Example 7

Preparation of Poly(Methoxyethylene-Alt-Maleic Acid Mono (α-Methoxy-Poly(Ethylene oxide)) and mono-{2-[1-methyl-3-oxo-3-(2,6,6-trimethyl-cyclohex-3-enyl)-propylsulfanyl]-ethyl}ester)

Poly(methoxyethylene-alt-maleic anhydride (Gantrez® AN-119 BF, origin: ISP Technologies, 10 mmol) was dissolved in 40 ml of THF. A solution of 3-(2-hydroxy-ethylsulfanyl)-1-(2,6,6-trimethyl-cyclohex-3-enyl)-butan-1-one (8 mmol, prepared as described in Example 1a) and α-methoxy-poly(ethylene oxide) (PEO, 2 mmol, $M_n$=550 g/mol) in 30 ml of THF was added dropwise. Then, a solution of triethylamine (10 mmol) and DMAP (61 mg, 0.5 mmol, 5-mol %) in 30 ml of THF was added dropwise at 0° C. The medium was heated at 40° C. for 24 h. The polymer solution was diluted with methylene chloride and extracted with an aqueous solution of HCl (5%), dried over $Na_2SO_4$, filtered, concentrated and precipitated into pentane. The product has been obtained as a solid (m=4 g). Yield=75% with a conversion of 20-mol % of PEO and 50-mol % of 2-[1-methyl-3-oxo-3-(2,6,6-trimethyl-cyclohex-3-enyl)-propylsulfanyl]-ethyl ester.

$^1$H-NMR (MeOD): 5.54 (m, 1H); 5.45 (m, 1H); 4.18 (m, 3.5H); 3.63 (m, 66H); 3.54 (m, 4H); 3.42 (m, 4.5H); 3.35 (m, 8H); 3.30 (m, 4.5H); 2.97 (s, 4H); 2.80 (m, 3H); 2.68 (m, 1.5H); 2.46 (m, 1H); 2.31 (m, 1H); 2.01 (m, 3H); 1.69 (m, 1H); 1.08-0.81 (m, 7H);

$^{13}$C-NMR (MeOD): 214.45s; 150.46s; 140.71d; 132.90d; 125.33d; 108.22d; 73.69t; 72.98t; 71.58t; 71.42t; 71.37t; 73.69t; 65.05t; 63.76d; 62.76s; 62.25t; 59.14d; 59.11d; 56.40t; 56.17t; 47.53t; 42.74t; 40.35q; 35.71d; 34.10d; 32.96s; 30.21s; 21.32d; 21.18d; 9.31q;

IR: 3445m-2931m-2881w-2075w-2507w-1980w-1782w-1721s-1647m-1563m-1452m-1389m-1348m-1213m-1172s-1084s-1037m-948m-837m-792m-653m.

Example 8

Dynamic Headspace Analysis of the Release of a Perfuming Ingredient from the Invention's Copolymers Incorporated into a Consumer Product (Fabric Softener)

The use as perfuming ingredient of the present invention's copolymer has been tested in a fabric softening application using a fabric softener base with the following composition: Stepantex® VK90 (origin: Stepan) 16.5%, calcium chloride 0.2% and water 83.3%. The perfuming performance of the free odoriferous α,β-unsaturated ketone, aldehyde or carboxylic ester and of the invention's copolymer was compared on dry fabric after 1 and 3 days using dynamic headspace analysis.

In a beaker, 1 ml of a solution of poly(maleic anhydride) based copolymer prepared in Example 4 (204.2 mg in 10 ml of acetone) was added to 1.80 g of the homogenized fabric softener base and filled up with 600 g of demineralized cold tap water. Three cotton towels (EMPA cotton test cloth Nr. 221, origin: Eidgenössische Materialprüfanstalt (EMPA), pre-washed with an unperfumed detergent powder and cut to ca. 12×12 cm sheets) were added and agitated manually for 3 min, left standing for 2 min, then wrung out by hand and weighed to ensure a constant quantity of residual water. As a reference sample, 1 ml of a solution containing an equimolar amount of unmodified δ-damascone (87.2 mg in 10 ml of acetone) was added to another 1.80 g of the original fabric softener base which was treated as described above. All cotton towels were line-dried for 1 or 3 days, respectively.

To determine the headspace concentration of δ-damascone, one of the dry towels was put into a headspace sampling cell (internal volume ca. 160 ml), thermostatted at 25° C. and exposed to a constant air flow of 200 ml/min, respectively. The air was filtered through active charcoal and aspirated through a saturated solution of NaCl. During 15 min the volatiles were adsorbed onto a waste Tenax® cartridge, then during 15 min on a clean Tenax® cartridge. The sampling was repeated 7 times every 60 min (45 min trapping on the waste cartridge and 15 min on a clean cartridge). The cartridges were desorbed on a Perkin Elmer TurboMatrix ATD desorber coupled to a Carlo Erba MFC 500 gas chromatograph equipped with a J&W Scientific DB1 capillary column (30 m, i.d. 0.45 mm, film 0.42 μm) and a FID detector. The volatiles were analyzed using a two step temperature gradient starting from 70° C. to 130° C. at 3° C./min and then going to 260° C. at 25° C./min. The injection temperature was at 240° C., the detector temperature at 260° C. To quantify the amount of δ-damascone in the headspace, external standard calibrations were carried out using six different concentrations of δ-damascone in acetone (varying between $1.96 \times 10^{-6}$ and $9.26 \times 10^{-4}$ mol/l). 2 μl of each calibration solution were injected onto three clean Tenax® cartridges, respectively. All the cartridges were desorbed immediately under the same conditions as those resulting from the headspace sampling (see above).

The following amounts of δ-damascone were detected from the sample containing the copolymer prepared in Example 4 as compared to the reference sample with unmodified δ-damascone(between brackets). All values are averages of two measurements:

| Headspace sampling time [min] | Amount of δ-damascone after drying for 1 d [ng/L] | Amount of δ-damascone after drying for 3 d [ng/L] |
| --- | --- | --- |
| 30 | 10.5 (1.3) | 9.9 (0.4) |
| 90 | 29.1 (0.9) | 31.6 (0.5) |
| 150 | 40.0 (2.2) | 41.4 (0.8) |
| 210 | 41.3 (1.6) | 44.8 (0.8) |
| 270 | 42.8 (1.0) | 43.8 (0.6) |
| 330 | 43.6 (1.5) | 43.9 (1.4) |
| 390 | 44.1 (1.6) | 42.6 (1.0) |
| 450 | 45.2 (1.4) | 42.2 (0.8) |

The data show that the amount of δ-damascone in the headspace over dry fabric increased significantly in the presence of the invention's copolymer as compared to the unmodified free fragrance molecule. After sampling for 450 min, an increase of the headspace concentration by a factor of 30 was observed after 1 day and an increase by a factor of 50 after 3 days, thus illustrating the desired increase of long-lastingness obtained by using the copolymers according to the invention.

Example 9

Dynamic Headspace Analysis of the Release of a Perfuming Ingredient from the Invention's Copolymers Incorporated into a Consumer Product (Fabric Softener)

The use as perfuming ingredient of the present invention's copolymer has been tested in a fabric softening application as described above (Example 8) using a fabric softener base with the following composition: Stepantex® VL90A (origin:

Stepan) 16.50%, calcium chloride (10%) 0.60%, Proxel® GXL (origin: Arch Chemicals) 0.04% and water 82.86%. The perfuming performance of the free odoriferous α,β-unsaturated ketone, aldehyde or carboxylic ester and of the invention's copolymer was compared on dry fabric after 1 and 3 days using dynamic headspace analysis.

For the measurements poly(maleic anhydride) based copolymers prepared in Example 1 (68.7 mg), Example 2 (99.6 mg), Example 3 (18.5 mg) and Example 7 (41.3 mg, dissolved in 2 ml of demineralized water) as well as copolymers from WO 2007/007216 (Example 1 (3d)) (16.4 mg) and from WO 03/049666 (Example 6b) (35.5 mg, dissolved in 1 ml of THF) were each added (to give a roughly equimolar δ-damascone content) to 1.8 g of the fabric softener base and the samples were stirred for 1 h. The samples were then transferred to a beaker and filled up with 600 g of demineralized cold tap water, respectively. Two cotton towels (EMPA cotton test cloth Nr. 221, pre-washed with an unperfumed detergent powder and cut to ca. 12×12 cm sheets) were added and agitated manually for 3 min, left standing for 2 min, then wrung out by hand, weighed to ensure a constant quantity of residual water and analyzed as described above (Example 8). As a reference sample, an equimolar amount of unmodified δ-damascone (8.8 mg) was added to another 1.80 g of the original fabric softener base which was treated as described above (Example 8). All cotton towels were line-dried for 1 or 3 days, respectively.

To quantify the amount of δ-damascone in the headspace, external standard calibrations were carried out using four different concentrations of δ-damascone in acetone (varying between $1.06 \times 10^{-6}$ and $1.06 \times 10^{-3}$ mol/l). 2 µl of each calibration solution were injected onto three clean Tenax® cartridges, respectively. All the cartridges were desorbed immediately under the same conditions as those resulting from the headspace sampling (see above).

The following amounts of δ-damascone were detected from the sample containing the copolymer prepared in Examples 1-3, 7 or those of patent applications WO 2007/007216 and WO 03/049666 (single measurements) as compared to the reference sample with unmodified δ-damascone (average of three measurements).

Headspace data obtained after 1 day of drying:

| Headspace sampling time [min] | Amount of unmodified δ-damascone (reference) [ng/l] | Amount of δ-damascone from copolymer of Example 1 [ng/l] | Amount of δ-damascone from copolymer of Example 2 [ng/l] | Amount of δ-damascone from copolymer of Example 3 [ng/l] |
|---|---|---|---|---|
| 30  | 2.4 | 6.9  | 3.7 | 3.2  |
| 90  | 2.4 | 18.5 | 3.8 | 7.1  |
| 150 | 3.2 | 22.1 | 5.1 | 8.1  |
| 210 | 3.2 | 22.8 | 4.0 | 10.2 |
| 270 | 2.7 | 24.1 | 3.8 | 10.3 |
| 330 | 2.2 | 23.5 | 4.0 | 10.4 |
| 390 | 2.7 | 24.5 | 4.6 | 11.2 |
| 450 | 2.6 | 24.1 | 4.8 | 12.1 |

Headspace data obtained after 3 days of drying:

| Headspace sampling time [min] | Amount of unmodified δ-damascone (reference) [ng/l] | Amount of δ-damascone from copolymer of Example 1 [ng/l] | Amount of δ-damascone from copolymer of Example 2 [ng/l] | Amount of δ-damascone from copolymer of Example 3 [ng/l] |
|---|---|---|---|---|
| 30  | 2.9 | 23.3 | 3.6 | 4.1  |
| 90  | 2.7 | 54.7 | 5.1 | 9.2  |
| 150 | 2.6 | 89.1 | 7.0 | 10.9 |
| 210 | 2.0 | 77.0 | 6.4 | 9.8  |
| 270 | 1.8 | 57.1 | 6.5 | 9.7  |
| 330 | 1.6 | 45.8 | 6.0 | 9.3  |
| 390 | 2.8 | 41.3 | 6.2 | 10.5 |
| 450 | 2.1 | 39.6 | 5.7 | 11.7 |

Headspace data obtained after 3 days of drying:

| | | Present invention | | Prior art | |
|---|---|---|---|---|---|
| Headspace sampling time [min] | * Reference [ng/l] | ** copolymer Example 7 [ng/l] | ** copolymer Example 4 [ng/l] | ** copolymer WO 07/007216 Example 1 (3d) [ng/l] | ** copolymer WO 03/049666 Example 6b [ng/l] |
| 30  | 2.9 | 8.8  | 9.9  | 5.9  | 3.0 |
| 90  | 2.7 | 18.2 | 31.6 | 6.2  | 6.5 |
| 150 | 2.6 | 23.7 | 41.4 | 11.2 | 7.5 |
| 210 | 2.0 | 28.6 | 44.8 | 11.7 | 6.8 |
| 270 | 1.8 | 31.8 | 43.8 | 13.2 | 6.6 |
| 330 | 1.6 | 33.3 | 43.9 | 13.6 | 6.4 |
| 390 | 2.8 | 32.7 | 42.6 | 14.3 | 6.6 |
| 450 | 2.1 | 34.6 | 42.2 | 12.2 | 8.7 |

* Amount of δ-damascone
** Amount of δ-damascone released from

The data show that the amount of δ-damascone in the headspace over dry fabric increased significantly in the presence of the invention's poly(maleic anhydride) based copolymers as compared to the unmodified free fragrance molecule (reference). The measured headspace concentrations furthermore show the particular slow release effect of the copolymers prepared in Examples 1 and 2 where even higher headspace concentrations were measured after 3 days than after 1 day.

Polymers with comparable amounts of grafted δ-damascone and free carboxylic acid functions in the backbone, such as for example the poly(maleic anhydride) based copolymer of the present Example 4 (see Example 8) and the polymethacrylate from WO 2007/007216 (Example 1 (3d))), have similar polarity and/or hydrophilic. A comparison of the behaviors of this two types of polymers shows clearly that the poly(maleic anhydride) based copolymers show a better release performance.

Modifying the polarity of the polymer (for example by grafting poly(ethylene oxide) moieties on the poly(maleic anhydride) backbone also can influence the release properties. The comparison of the headspace concentrations measured for the poly(maleic anhydride) based copolymer of present Example 7 with those obtained with the polymethacrylate from WO 2007/007216 (Example 1 (3d)) or with the polystyrene from WO 03/049666 (Example 6b) shows an increased performance of the poly(maleic anhydride) based copolymer of the present invention.

Furthermore, the direct olfactive comparison of the cotton towels treated with poly(maleic anhydride) based copolymer of Example 7 with the polystyrene from WO 03/049666 (Example 6b) two days after the headspace sampling still revealed a strong damascone type odor in the former case and a much less pronounced smell in the latter case.

The release efficiency and/or the dispersibility of the polymers in water can be modulated by adjusting the polarity of the polymer backbone. The poly(maleic anhydride) based copolymers of Example 4 (with a methoxy group containing comonomer, see Example 8) and of Example 7 are for example more polar than those of Examples 2 and 3 (with hydrophobic isobutylene or ethylene comonomers, respectively).

Besides polarity effects of the comonomer, the deposition of the polymers on the fabric is another important aspect to be considered. It is known that hydrophobic materials are more efficiently deposited on fabrics. Therefore, we attribute the good performance of the poly(maleic anhydride) based copolymer of Example 1 as compare to those of Examples 2 and 3 to an increased surface deposition of the former with respect to the latter.

For comparable amounts of δ-damascone on the polymer and/or for similar polarities of the polymers, the poly(maleic anhydride) based copolymers of the present invention show better release properties than other prior art polymers. A good balance between hydrophobicity (good deposition, lower dispersion in aqueous media) and hydrophilicity (lower deposition, good dispersion in aqueous media) is an important criterion for the choice of the appropriate material with respect to the targeted application.

Example 10

Olfactive Evaluation of the Release of a Perfuming Ingredient from the Invention's Copolymers Incorporated into a Consumer Product (Fabric Softener)

The tests were carried out using a standard fabric softener base, generally used to treat terry towels.

The fabric softener base with the following final composition has been prepared: Stepantex® VK90 (origin: Stepan) 16.5%, calcium chloride 0.2% and water 83.3%. The washing of the terry towels was carried out with 85 g of an un-perfumed detergent base (VIA, origin: Unilever), followed by a rinsing cycle using 35 g of the above described softener base to which were previously added 0.5 mmol of pure δ-damascone or, alternatively, the corresponding molar amount of δ-damascone releasing copolymer prepared in Example 4.

A washing machine (Miele Novotronic W300-33CH) was loaded with 10 small terry towels (18 cm*18 cm, about 30 g each) and 2 kg of large cotton towels. The load was washed at 40° C. using a short cycle program and a rinsed at 900 rpm.

At the end of the washing, the 17 small terry towels were line-dried for 24 h and wrapped into aluminium foil for storage, before being evaluated in intensity and assessment by 20 panelists after 3 and 7 d, using a scale ranging from "1" (no odor) to "10" (very strong).

The following average intensity and freshness (between brackets) for the different samples were determined:

| Tested molecule | Evaluation after 3 days | Evaluation after 7 days |
| --- | --- | --- |
| δ-damascone (reference) | 3.24 (3.01) | 2.86 (2.82) |
| Copolymer of Example 4 | 5.75 (4.83) | 5.75 (5.36) |

The evaluation showed significant differences in intensity for the comparison of the two samples (with >99.9% of statistical significance). The towels containing the copolymer according to the invention was found to be stronger and fresher than the reference sample. Whereas the intensity of the reference decreased with time, the intensity of the fragrance for sample containing the copolymer remained constant.

The invention claimed is:

1. A co-polymer, for releasing in a controlled manner an odoriferous α,β-unsaturated ketone, aldehyde or carboxylic ester, and comprising at least one repeating unit of formula

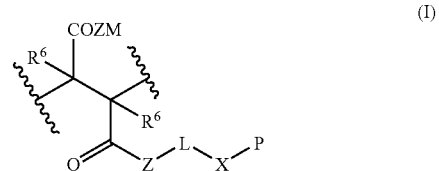

(I)

wherein
P represents a radical susceptible of generating an odoriferous α,β-unsaturated ketone, aldehyde or carboxylic ester and is represented by formula

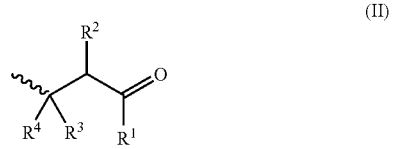

(II)

in which the wavy line indicates the location of the bond between said P and X;

$R^1$ represents a hydrogen atom, a $C_1$ to $C_6$ alkoxyl radical or a $C_1$ to $C_{15}$ linear, cyclic or branched alkyl, alkenyl or alkadienyl radical, optionally substituted by $C_1$ to $C_4$ alkyl groups; and $R^2$, $R^3$ and $R^4$ represent a hydrogen atom, a $C_6$ to $C_{10}$ aromatic ring or a $C_1$ to $C_{15}$ linear, cyclic or branched alkyl, alkenyl or alkadienyl radical, optionally substituted by $C_1$ to $C_4$ alkyl groups;

or two, or three, of the groups $R^1$ to $R^4$ are bound together to form a saturated or unsaturated ring having 5 to 20 carbon atoms and, including the carbon atom to which said $R^1$, $R^2$, $R^3$ or $R^4$ groups are bound, this ring being optionally substituted by $C_1$ to $C_8$ linear, branched or cyclic alkyl or alkenyl groups;

X represents a functional group selected from the group consisting of the formulae i) to v):

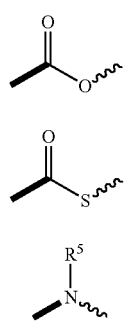

in which formulae wavy lines indicate bonds between P and X and the bold lines indicate the location of the bond between said X and L, and $R^5$ represents a hydrogen atom or a $C_1$-$C_4$ alkyl group;

L represents a $C_2$-$C_{15}$ hydrocarbon group optionally comprising from 1 to 10 oxygen, sulfur or nitrogen atoms;

Z represents an oxygen or sulfur atom or a $NR^5$ group, $R^5$ representing a hydrogen atom or a $C_1$-$C_4$ alkyl group;

the $R^6$ groups represent independently of each other a hydrogen atom or a $C_1$-$C_4$ hydrocarbon group; and M represents a hydrogen atom, an alkali or earth alkali metal ion if Z represents an oxygen or sulfur atom or a hydrogen atom if Z represents a $NR^5$ group.

2. A co-polymer according to claim 1, wherein P represents a radical of the formulae (P-1) to (P-11), in the form of any one of its isomers:

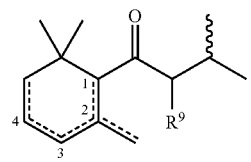

(P-1)

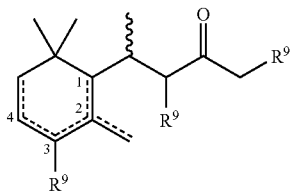

(P-2)

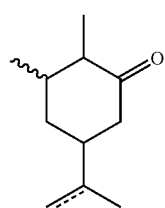

(P-3)

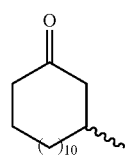

(P-4)

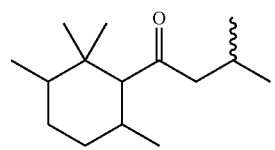

(P-5)

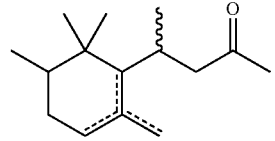

(P-6)

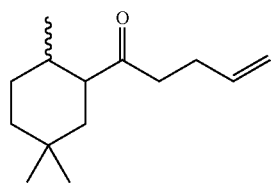

(P-7)

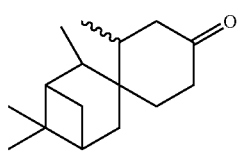

(P-8)

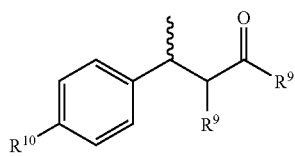

(P-9)

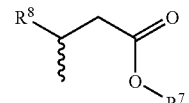

(P-10)

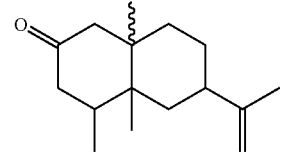

(P-11)

in which formulae wavy lines indicate bonds between P and X and the dotted lines represent a single or double bond, $R^7$ indicating a methyl or ethyl group, $R^8$ representing a $C_6$ to $C_9$ linear or branched alkyl, alkenyl or alkadienyl group, $R^9$ being a hydrogen atom or a methyl group and $R^{10}$ representing a hydrogen atom, a hydroxy or methoxy group or a $C_1$-$C_4$ linear or branched alkyl group.

3. A co-polymer according to claim 1, wherein X represents a functional group selected from the group consisting of the formulae i) to iii)

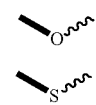

i)

ii)

-continued

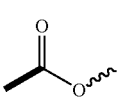

iii)

as defined in claim 1.

4. A co-polymer according to claim 1, wherein Z represents an oxygen atom.

5. A co-polymer according to claim 1, further comprising a repeating unit of the formula (III)

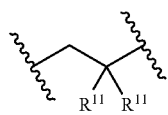

(III)

wherein the $R^{11}$ groups represent independently of each other
a hydrogen or halide atom;
a $C_1$-$C_6$ hydrocarbon group optionally comprising from 1 to 4 heteroatoms selected from the group consisting of oxygen and sulfur atoms;
a carboxylic group of formula $COOR^{12}$ wherein $R^{12}$ represents a hydrogen atom, a $C_1$-$C_{60}$ alkyl or alkenyl group optionally comprising from 1 to 30 oxygen atoms;
a $OR^{13}$ group, wherein $R^{13}$ represents a hydrogen atom, a $C_1$-$C_6$ alkyl group or a $COR^{14}$ group, $R^{14}$ representing a $C_1$-$C_6$ alkyl group; or
a pyrrolidone unit, connected by the nitrogen atom;
or of the formula (IV)

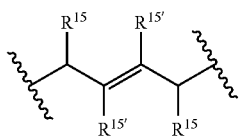

(IV)

wherein the groups $R^{15}$ or $R^{15'}$ represent a hydrogen atom or methyl or ethyl group, the two $R^{15}$ can be bonded together and represent an oxygen atom or a $CH_2O$ group.

6. A co-polymer according to claim 1, wherein said co-polymer releases an odoriferous α,β-unsaturated ketone, aldehyde or carboxylic ester selected from the group consisting of β-damascenone, damascones, ionones, 2-cyclopentadecen-1-one, 1-(5,5-dimethyl-1-cyclohexen-1-yl)-4-penten-1-one, 1(6),8-p-menthadien-2-one, 1-(2,2,3,6-tetramethyl-1-cyclohexyl)-2-buten-1-one and 4-(2,2,3,6-tetramethyl-1-cyclohexyl)-3-buten-2-one.

7. A co-polymer according to claim 1, obtained by a process comprising the following steps:
A) reacting together:
a co-polymer obtained by reacting together at least one olefin of formula $CH_2\!\!=\!\!CR^{11}{}_2$, with the $R^{11}$ groups representing independently of each other:
a hydrogen or halide atom;
a $C_1$-$C_6$ hydrocarbon group optionally comprising from 1 to 4 heteroatoms selected from the group consisting of oxygen and sulfur atoms;
a carboxylic group of formula $COOR^{12}$ wherein $R^{12}$ represents a hydrogen atom, a $C_1$-$C_{60}$ alkyl or alkenyl group optionally comprising from 1 to 30 oxygen atoms;
a $OR^{13}$ group, wherein $R^{13}$ represents a hydrogen atom, a $C_1$-$C_6$ alkyl group or a $COR^{14}$ group, $R^{14}$ representing a $C_1$-$C_6$ alkyl group; or
a pyrrolidone unit, connected by the nitrogen atom;
or of the formula (IV)

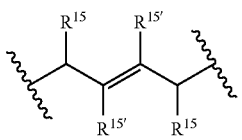

(IV)

wherein the groups $R^{15}$ or $R^{15'}$ represent a hydrogen atom or methyl or ethyl group, the two $R^{15}$ can be bonded together and represent an oxygen atom or a $CH_2O$ group; and at least a derivative of formula

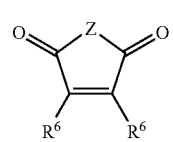

(VI)

wherein the $R^6$ groups and Z have the same meaning as indicated above; and
a compound of formula P—X-L-Z-M, wherein P, X, L, Z and M have the same meaning indicated in claim 1; and B) hydrolyzing all or part of the unreacted anhydride functional group of the polymerized monomer (VI) of the co-polymer with an alcohol of formula $R^xOH$, wherein $R^x$ represents a $C_1$-$C_4$ alkyl group or a polyether having a molecular weight of between 100 and 4000 g/mol; and/or C) optionally reacting the co-polymer obtained in step A) or B) with a base.

8. A co-polymer according to claim 7, wherein P is a radical selected from the group consisting of the formulae (P-1), (P-2), (P-3), (P-4), (P-5), (P-6), (P-7), (P-8), (P-9), (P-10), (P-11), in the form of any one of its isomers:

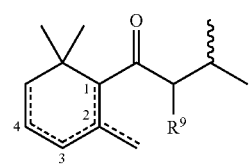

(P-1)

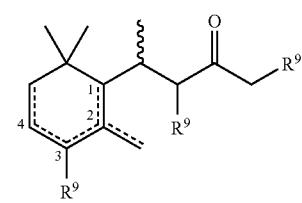

(P-2)

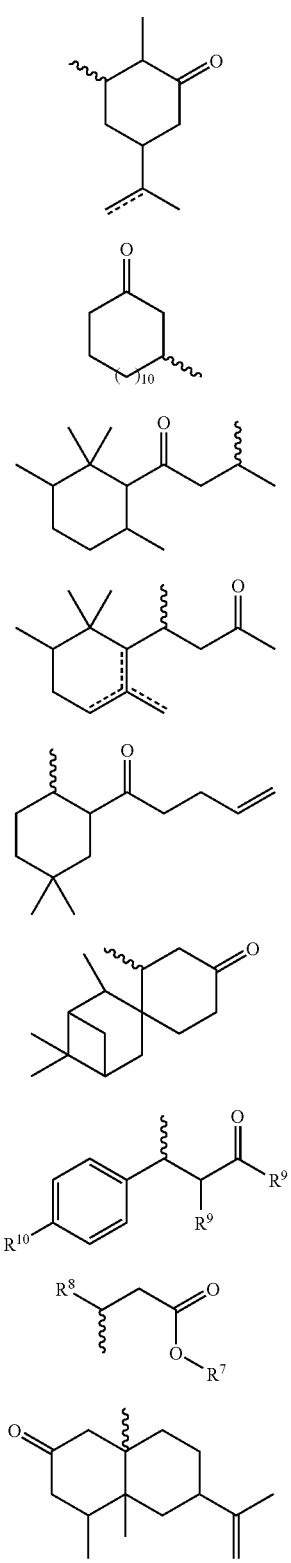

in which formulae wavy lines indicate bonds between P and X and the dotted lines represent a single or double bond, $R^7$ indicating a methyl or ethyl group, $R^8$ representing a $C_6$ to $C_9$ linear or branched alkyl, alkenyl or alkadienyl group, $R^9$ being a hydrogen atom or a methyl group and $R^{10}$ representing a hydrogen atom, a hydroxy or methoxy group or a $C_1$-$C_4$ linear or branched alkyl group;

X represents a sulfur atom;

L represents a linear, branched or cyclic saturated or unsaturated $C_2$-$C_6$ group;

Z represents an oxygen atom;

M represents a sodium, potassium, calcium, magnesium or hydrogen atom; and the copolymer is one obtained by the co-polymerization of maleic anhydride and an olefin selected from the group consisting of 1-octadecene, ethylene, isobutylene or methoxyethylene.

9. A perfuming composition comprising:

i) as a perfuming ingredient, at least one co-polymer, for releasing in a controlled manner an odoriferous α,β-unsaturated ketone, aldehyde or carboxylic ester, and comprising at least one repeating unit of formula

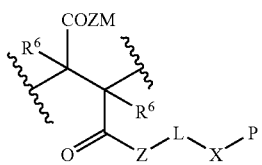

(I)

wherein

P represents a radical susceptible of generating an odoriferous α,β-unsaturated ketone, aldehyde or carboxylic ester and is represented by formula

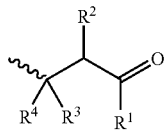

(II)

in which the wavy line indicates the location of the bond between said P and X;

$R^1$ represents a hydrogen atom, a $C_1$ to $C_6$ alkoxyl radical or a $C_1$ to $C_{15}$ linear, cyclic or branched alkyl, alkenyl or alkadienyl radical, optionally substituted by $C_1$ to $C_4$ alkyl groups; and $R^2$, $R^3$ and $R^4$ represent a hydrogen atom, a $C_6$ to $C_{10}$ aromatic ring or a $C_1$ to $C_{15}$ linear, cyclic or branched alkyl, alkenyl or alkadienyl radical, optionally substituted by $C_1$ to $C_4$ alkyl groups; or two, or three, of the groups $R^1$ to $R^4$ are bound together to form a saturated or unsaturated ring having 5 to 20 carbon atoms and, including the carbon atom to which said $R^1$, $R^2$, $R^3$ or $R^4$ groups are bound, this ring being optionally substituted by $C_1$ to $C_8$ linear, branched or cyclic alkyl or alkenyl groups;

X represents a functional group selected from the group consisting of the formulae i) to v):

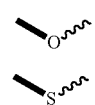

-continued

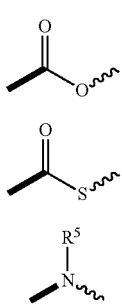
iii)

iv)

v)

in which formulae wavy lines indicate bonds between P and X and the bold lines indicate the location of the bond between said X and L, and $R^5$ represents a hydrogen atom or a $C_1$-$C_4$ alkyl group;

L represents a $C_2$-$C_{15}$ hydrocarbon group optionally comprising from 1 to 10 oxygen, sulfur or nitrogen atoms;

Z represents an oxygen or sulfur atom or a $NR^5$ group, $R^5$ representing a hydrogen atom or a $C_1$-$C_4$ alkyl group;

the $R^6$ groups represent independently of each other a hydrogen atom or a $C_1$-$C_4$ hydrocarbon group; and M represents a hydrogen atom, an alkali or earth alkali metal ion if Z represents an oxygen or sulfur atom or a hydrogen atom if Z represents a $NR^5$ group;

ii) at least one ingredient selected from the group consisting of a perfumery carrier and a perfumery base; and iii) optionally at least one perfumery adjuvant.

10. A perfumed article comprising:

i) as a perfuming ingredient, at least one co-polymer, for releasing in a controlled manner an odoriferous $\alpha,\beta$-unsaturated ketone, aldehyde or carboxylic ester, and comprising at least one repeating unit of formula

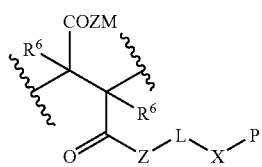
(I)

wherein

P represents a radical susceptible of generating an odoriferous $\alpha,\beta$-unsaturated ketone, aldehyde or carboxylic ester and is represented by formula

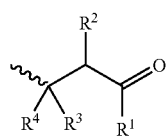
(II)

in which the wavy line indicates the location of the bond between said P and X;

$R^1$ represents a hydrogen atom, a $C_1$ to $C_6$ alkoxyl radical or a $C_1$ to $C_{15}$ linear, cyclic or branched alkyl, alkenyl or alkadienyl radical, optionally substituted by $C_1$ to $C_4$ alkyl groups; and $R^2$, $R^3$ and $R^4$ represent a hydrogen atom, a $C_6$ to $C_{10}$ aromatic ring or a $C_1$ to $C_{15}$ linear, cyclic or branched alkyl, alkenyl or alkadienyl radical, optionally substituted by $C_1$ to $C_4$ alkyl groups; or two, or three, of the groups $R^1$ to $R^4$ are bound together to form a saturated or unsaturated ring having 5 to 20 carbon atoms and, including the carbon atom to which said $R^1$, $R^2$, $R^3$ or $R^4$ groups are bound, this ring being optionally substituted by $C_1$ to $C_8$ linear, branched or cyclic alkyl or alkenyl groups;

X represents a functional group selected from the group consisting of the formulae i) to v):

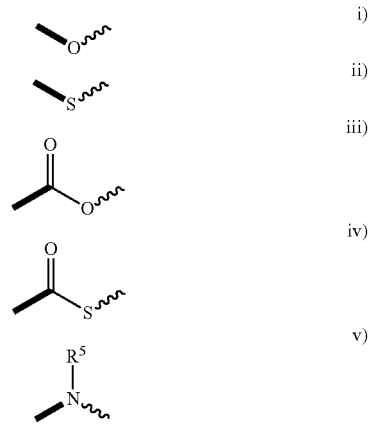

in which formulae the wavy lines are indicate bonds between P and X and the bold lines indicate the location of the bond between said X and L, and $R^5$ represents a hydrogen atom or a $C_1$-$C_4$ alkyl group;

L represents a $C_2$-$C_{15}$ hydrocarbon group optionally comprising from 1 to 10 oxygen, sulfur or nitrogen atoms;

Z represents an oxygen or sulfur atom or a $NR^5$ group, $R^5$ representing a hydrogen atom or a $C_1$-$C_4$ alkyl group;

the $R^6$ groups represent independently of each other a hydrogen atom or a $C_1$-$C_4$ hydrocarbon group; and M represents a hydrogen atom, an alkali or earth alkali metal ion if Z represents an oxygen or sulfur atom or a hydrogen atom if Z represents a $NR^5$ group;

ii) a consumer product base.

11. A perfumed article according to claim 10, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

12. A co-polymer according to claim 7, wherein in step B) of the process, $R^x$ is methyl or ethyl.

\* \* \* \* \*